Figure 1:
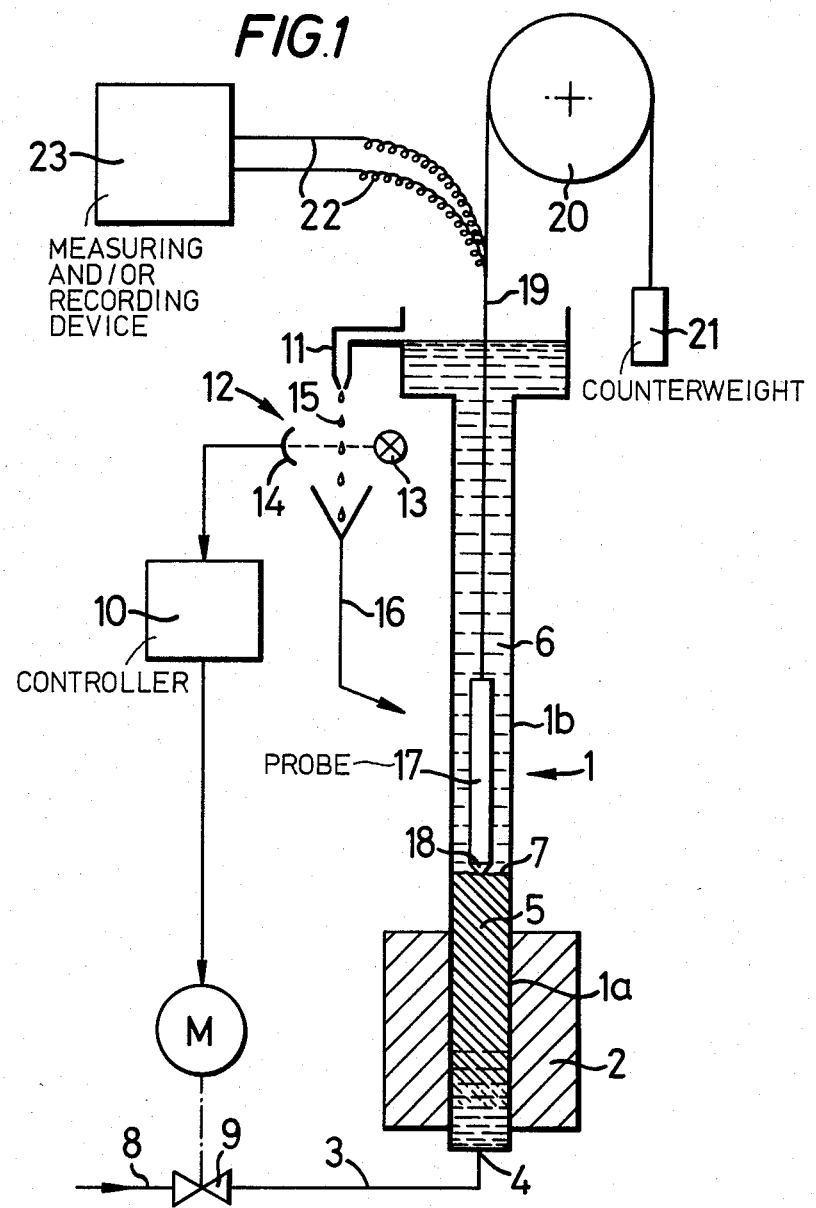

United States Patent [19]

Croo

[11] Patent Number: 4,508,460
[45] Date of Patent: Apr. 2, 1985

[54] PROCESS AND APPARATUS FOR CONTINUOUS MEASUREMENT OF THE POUR POINT OF OIL

[75] Inventor: Robert J. Croo, Dubkerque, France

[73] Assignee: The British Petroleum Company p.l.c., London, England

[21] Appl. No.: 465,355

[22] Filed: Feb. 9, 1983

[30] Foreign Application Priority Data

Feb. 11, 1982 [FR] France .............. 82 02261

[51] Int. Cl.³ ........................... G01N 25/04
[52] U.S. Cl. ........................ 374/16; 62/139; 73/321
[58] Field of Search ............ 374/16, 18, 22, 24; 62/139

[56] References Cited

U.S. PATENT DOCUMENTS

| | | | |
|---|---|---|---|
| 1,307,601 | 6/1919 | Saunders | 374/24 X |
| 2,600,341 | 6/1952 | Thompson | 73/321 |
| 3,150,515 | 9/1964 | Malina | 374/16 |
| 3,173,288 | 3/1965 | Davis et al. | 374/16 X |
| 3,173,289 | 3/1965 | Davis | 62/139 X |
| 3,442,116 | 5/1969 | Brown | 374/16 X |
| 3,496,760 | 2/1970 | Puzniak | 374/16 |
| 3,580,047 | 5/1971 | Simpson | 374/22 |
| 4,024,753 | 5/1977 | Ouvrard | 374/24 |

FOREIGN PATENT DOCUMENTS

| | | | |
|---|---|---|---|
| 1237096 | 6/1971 | United Kingdom | 374/16 |
| 171668 | 7/1964 | U.S.S.R. | 374/24 |

Primary Examiner—Daniel M. Yasich
Attorney, Agent, or Firm—Morgan, Finnegan, Pine, Foley & Lee

[57] ABSTRACT

A process for continuously measuring the pour point of oil comprises introducing the oil into the lower portion of a substantially vertical tube at a pressure sufficient to cause the oil to move up the tube and subjecting the oil to a temperature gradient as it rises through the tube such that the oil is cooled in the lower portion of the tube to a temperature below the pour point and solidifies, and in the upper portion of the tube the temperature of the oil is raised so that the oil becomes liquid again thereby forming a solid/liquid interface in the tube. A temperature sensing means which is axially moveable in the tube is arranged to rest at the solid/liquid interface and provides a continuous signal, representing the pour point of the oil sample at the interface to a measuring and/or recording device. The invention also includes apparatus for carrying out the process.

7 Claims, 2 Drawing Figures

PROCESS AND APPARATUS FOR CONTINUOUS MEASUREMENT OF THE POUR POINT OF OIL

The present invention relates to a process and apparatus for the continuous measurement of the pour point of oil.

The French standard test method NF. T60.105 defines the pour point of an oil as being "the lowest temperature at which the oil will still flow, when it is cooled, without agitation, under standardised conditions."

Methods and apparatus for measuring pour point are known and methods have been proposed which may be carried out automatically. For example, U.S. Pat. No. 3,580,047 discloses apparatus for measuring pour point by observing the temperature at which the solidified constituents of an oil sample, upon heating, will no longer support a small object. The method comprises introducing a sample of oil into the apparatus and cooling the oil until it crystallises and then slowly re-heating the sample during which heating step the temperature of the oil is measured and a check is made of the temperature at which a small object in the vicinity of the temperature sensing device is no longer supported by the solidified oil. It is then necessary to re-heat and drain the apparatus of the oil sample before introducing another sample and repeating the method. The patent discloses apparatus for automatically carrying out the method. However, the automation of the various liquid movements and the cooling and heating operations and also of the lifting and releasing of the small object is somewhat complex. The successive pour point measurements are therefore relatively widely spaced in time. For some applications, e.g. for oil leaving a production unit, it would be useful to be able to continuously measure the pour point of the oil. This cannot be achieved using the known sequential methods.

The applicants have invented a relatively simple process for continuously measuring the pour point of oil and apparatus for carrying out the method.

Thus according to the present invention a process for continuously measuring the pour point of oil comprises introducing a continuous flow of an oil sample into a substantially vertical tube, which tube has smooth internal surfaces and a substantially constant bore, the liquid (b) a cooler associated with the lower portion of the tube;

(c) a temperature sensing means which is axially moveable in the tube;

(d) a measuring and/or recording device for displaying and/or recording the temperature indicated by the temperature sensing means.

Figure 2:
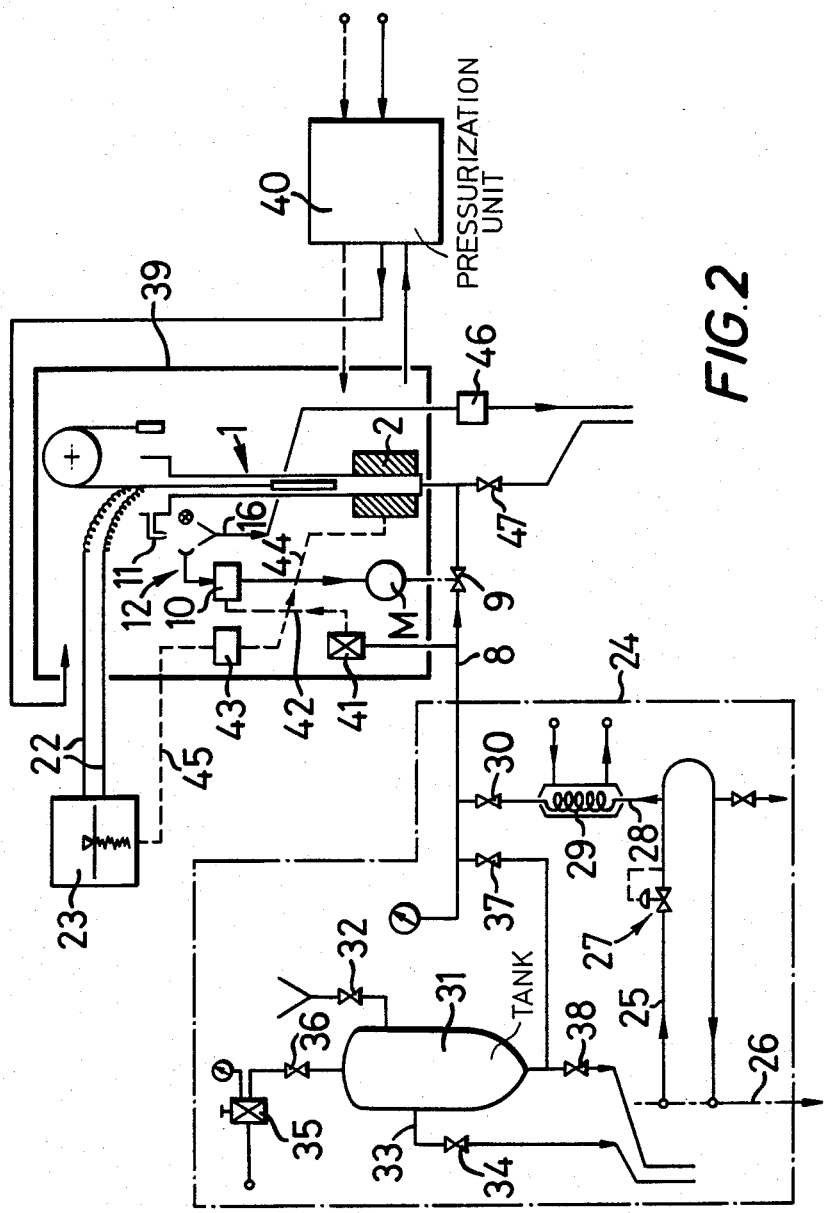

The invention will be described with reference to one embodiment of the invention illustrated in the accompanying drawings FIGS. 1 and 2 in which:

FIG. 1 is a schematic representation of apparatus according to the present invention and, FIG. 2 is a flow diagram illustrating how the apparatus of FIG. 1 may be used.

FIG. 1 shows a substantially vertical tube 1 having an inlet 4 in the lower portion 1a and an outlet 11 in the upper portion 1b. A cooler 2 is associated with the lower portion 1a of the tube. This cooler is capable of reducing the temperature of oil passing through the lower portion 1a to below the pour point of the oil. Preferably the cooler 2 is capable of reducing the oil to a temperature at least 10° C. below the minimum pour point which it is desired to measure. Any suitable cooling device may be used such as for example a propane evaporator or more preferably an electrical semiconductor cooling device.

The liquid oil sample from line 8 introduced into the lower portion 1a of the tube 1 via inlet 4 is at a sufficiently high pressure to cause the column of oil in the tube to rise up the tube and out of the outlet 11. As it rises through the lower portion 1a, the cooler 2 reduces the temperature of the oil to below its pour point and the oil solidifies. Preferably the cooler 2 reduces the oil sample to 10° C. below its pour point.

As the oil moves up the upper portion 1b it is reheated. Ambient temperature may be sufficient to heat the oil. Alternatively a heat supply may be associated with the upper portion 1b of the tube 1. As the oil temperature rises the solidified oil 5 becomes liquid 6 again. Thus a solid/liquid interface 7 is formed in the upper portion 1b of the tube.

The temperature of the oil sample at the interface 7 represents the pour point of the oil according to the definition in NF. T60.105. This temperature is measured using a probe 17 having a temperature sensing means 18

The temperature measuring and/or recording device 23 may be a known device for displaying and/or recording the temperature indicated by the temperature sensing means 18.

The pressure of the oil entering the tube 1 at inlet 4 must be sufficient to cause the column of oil, including the solidified oil, to move up the tube. In order to assist this movement, the internal surfaces of the tube 1 should be smooth and the bore of the tube should be substantially constant.

The maximum flowrate of the oil is determined inter alia by the ability of the cooler to reduce the temperature of the oil to below its pour point as it passes through the lower portion 1a of the tube. Typically the flowrate may be of the order of 0.5 to 1.0 $cm^3$ per minute.

In FIG. 1 the flowrate of the oil to the tube 1 via line 3 is regulated by an automatic control valve 9 which may be a motorised needle valve. The servo-motor M of the valve 9 is controlled by a controller 10 associated with a device 12 for measuring the flowrate of the oil through the tube 1.

The device 12 shown in FIG. 1 for measuring the flowrate of the oil through the tube 1 comprises a light source 13 and a cell 14 which together count the drops of oil 15 dripping from the outlet 11 as they pass between the light source 13 and the cell 14 before falling into a drain 16.

The controller 10 may be an electronic device comprising a time base and a reference value in the form of a desired number of drops per minute. The controller 10 regulates the valve 9 in order to bring the measured flowrate to within certain limits of the reference value.

It has been found convenient to measure the flowrate through the tube 1 by measuring the amount of oil passing out of the outlet 11 using a device as described above. However, the flowrate may be measured at other positions using other, known apparatus.

An example of how the apparatus for continuously measuring pour point may be used is illustrated with refer to FIG. 2.

The sampling apparatus 24 shown in FIG. 2 illustrates how oil samples may be taken from a continuous flow of oil such as, for example, a line 26 from a production unit, or from a static source such as a tank 31. The two potential oil sources are arranged so that oil from one source or the other may be supplied to line 8.

Line 26 diagramatically represents a continuous flow of oil such as for example a line from a production unit. A sample loop 25 takes oil from line 26, the flowrate being controlled by a pressure regulator 27. The oil sample passes through line 28 to a cooling coil 29, cooled by water, before passing through a non-return valve 30 into line 8.

The second oil source comprises a tank 31. Valve 32 controls the flow of oil into the tank 31. Line 33 is an overflow controlled by valve 34. The oil in the tank 31 may be placed under pressure by closing valves 32 and 34 and introducing a gas e.g. air supplied via a pressure reducing filter 35 and a valve 36. The oil under pressure may be discharged via non-return valve 37 to line 8. Valve 38 allows the tank to be drained.

The sampling apparatus may comprise a number of sources and various known methods may be used to ensure that the oil sample is supplied to line 8 at a sufficient pressure.

The pour point measuring apparatus may be enclosed in a cabinet 39 which, for reasons of safety, may be pressurised e.g. to about 10 millibars in accordance with known techniques by a pressurisation unit 40.

The apparatus shown in FIG. 2 illustrates a number of ways of improving the control of the basic apparatus as illustrated in FIG. 1.

As described above with reference to FIG. 1, the valve 9 is opened or closed depending on the flowrate through the tube 1. Thus, an interruption in the oil supply would result in no flow through the tube and the controller 10 would open valve 9 fully. Similarly a momentary drop in pressure would open the valve. When the flow of oil is resumed or the pressure returns to normal, the open valve may cause the tube to overflow. In FIG. 2, a pressure measuring device 41 is used to measure the pressure of oil in line 8. The signal from the pressure measuring device 41 to the controller 10 is carried by connection 42. The controller 10 closes valve 9 if the pressure falls below a predetermined value e.g. 2 bar. Thus the risk of overflow is reduced.

The apparatus illustrated in FIG. 2 includes a control loop which regulates the cooling device so that it cools the oil in the lower portion of the tube 1 to a temperature which is a predetermined amount lower than the pour point as detected by the temperature sensing device. The control loop comprises a controller 43 which uses a signal from the measuring/recording device 23 carried by connection 45 to determine the signal to be sent by connection 44 to control the temperature of the cooler 2. Suitably controller 43 controls the cooler 2 so that the temperature of the oil is reduced to 10° C. lower than the temperature of the pour point as measured by device 23. The pour point of oil is generally from −35° C. to 10° C. and so the cooler is preferably capable of cooling oil from −45° C. to 0° C. This control loop maintains the solid/liquid interface at a relatively constant position in the tube thereby reducing the amplitude of movement of the probe 17 and temperature sensing device 18 and also limiting the length of the upper portion 1b required.

The drain 16 for the oil leaving the apparatus passes through a hydraulic protection device 46 to maintain the pressurisation of the cabinet 39. Valve 47 enables the tube to be drained.

I claim:

1. A process for continuously measuring the pour point of oil comprising
  A. introducing a continuous flow of an oil sample into a substantially vertical tube, which tube has smooth internal surfaces and a substantially constant bore, the liquid oil being introduced in the lower portion of the tube at a pressure which is sufficient to cause the oil in the tube to move upwards through the tube and out via an outlet in the upper portion of the tube;
  B. cooling the oil as it moves upwards through the lower portion of the tube, by cooling means associated with the lower portion of the tube, to a temperature below the pour point of the oil so that the oil solidifies;
  C. increasing the temperature of the oil as it moves upwards through the upper portion of the tube to a temperature sufficiently above the pour point of the oil so that the solidified oil becomes liquid again thereby forming a solid/liquid interface in the tube;
  D. positioning a temperature sensing means at the solid/liquid interface to provide a continuous signal, representing the pour point of the oil sample at the interface, to a measuring and/or recording device and E. providing means for moving the temperature sensing means within the tube so that it remains at the solid/liquid interface.

2. Apparatus for continuously measuring the pour point of oil comprising

A. a substantially vertical tube having an inlet in the lower portion of the tube and an outlet in the upper portion of the tube, the tube having smooth internal surfaces and a substantially constant bore;

B. a cooler associated with the lower portion of the tube;

C. a temperature sensing means;

D. means for moving the temperature sensing means within the tube which means positions the temperature sensing means at the solid/liquid interface of the oil, said interface being formed within the tube when the apparatus is in use and E. a measuring and/or recording device for displaying and/or recording the temperature indicated by the temperature sensing means.

3. Apparatus for continuously measuring the pour point of oil comprising

A. a substantially vertical tube having an inlet in the lower portion of the tube and an outlet in the upper portion of the tube, the tube having smooth internal surfaces and a substantially constant bore;

B. a cooler associated with the lower portion of the tube;

C. a temperature sensing means;

D. means for moving the temperature sensing means within the tube which means comprises a probe to which the temperature sensing means is attached, the probe being suspended in the tube and counterbalanced by means so that when the apparatus is in use the temperature sensing means is positioned at the solid/liquid interface of the oil which is formed within the tube and the weight of the probe bearing down on the solidified oil is reduced by the counterbalnace means and E. a measuring and/or recording device for displaying and/or recording the temperature indicated by the temperature sensing means.

4. Apparatus as claimed in claim 2 or claim 3 in which the cooler is regulated to cool the oil in the tube to a temperature which is a predetermined amount lower than the pour point as detected by the temperature sensing means.

5. Apparatus as claimed in claim 2 or claim 3 in which the cooler is an electrical semiconductor cooling device.

6. Apparatus as claimed in claim 2 or claim 3 in which the flowrate of the oil into the tube is controlled by an automatic control valve cooperating with a device for measuring the flowrate of oil leaving the tube via the outlet.

7. Apparatus as claimed in claim 2 or claim 3 in which the flowrate of the oil into the tube is controlled by an automatic control valve cooperating with a device for measuring the flowrate of oil leaving the tube via the outlet the control valve being connected to means for measuring the pressure of the oil supplied to the tube via means for closing the valve when the measured pressure falls below a predetermined valve.

* * * * *